US006506885B1

(12) United States Patent
Beier

(10) Patent No.: US 6,506,885 B1
(45) Date of Patent: Jan. 14, 2003

(54) MONOCLONAL ANTIBODIES TO THE DRUG TILMICOSIN AND A METHOD FOR DETECTING THE SAME

(75) Inventor: Ross C. Beier, College Station, TX (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 09/964,980

(22) Filed: Sep. 27, 2001

(51) Int. Cl.[7] ......................... C07K 17/02; C12P 21/08; C12N 5/06; G01N 33/537; G01N 33/543

(52) U.S. Cl. .................... 530/405; 530/388.9; 530/403; 530/404; 530/405; 435/7.92; 435/7.93; 435/345; 435/810; 436/528; 436/548

(58) Field of Search ............................... 435/7.92, 7.93, 435/70.21, 345, 326, 810; 422/61; 436/528, 548, 86; 530/388.1, 388.9, 403, 404, 405; 514/30

(56) References Cited

PUBLICATIONS

Silverlight, J.J. et al., "Antisera to Tilmicosin for use in ELISA and for Immunohistochemistry", *Food and Agricultural Immunology*, vol. 11, 1999, pp. 321–328.

Wicker, Alan L., et al., "Particle Concentration Fluorescence Immunoassay for Determination of Tylosin in Premix, Feeds, and Liquid Feed Supplement: Comparison with Turbidimetric Assay", *Journal of AOAC International*, vol. 77, No. 1994, pp. 1083–1095.

Jackman, R. et al., "Development of Antibodies to Tilmicosin and their use in the Immunolocalization of the Antibiotic in Porcine Lung Tissue", *Journal of Veterinary Pharmacology and Therapeuties*, vol. 20 (supp. 1), 1997, pp. 131–132.

*Primary Examiner*—Mary E. Ceperley
*Assistant Examiner*—My Chau T Tran
(74) *Attorney, Agent, or Firm*—M. Howard Silverstein; Randall E. Deck; John D. Fado

(57) ABSTRACT

Hybridoma cell lines have been generated which produce and secrete monoclonal antibodies which selectively bind to tilmicosin. These hybridomas may be obtained by using as an immunization agent or immunogen, 23-deoxo-23-demycinosyl tilmicosin which has been conjugated to an immunogenic carrier. The antibodies may be used to detect and/or quantify tilmicosin in biological samples. The monoclonal antibodies also may be incorporated into kits.

19 Claims, No Drawings

MONOCLONAL ANTIBODIES TO THE DRUG TILMICOSIN AND A METHOD FOR DETECTING THE SAME

BACKGROUND OF THE INVENTION

1. Field of the Invention

This invention relates to hybridoma cell lines and monoclonal antibodies produced therefrom which may be used to detect tilmicosin.

2. Description of the Prior Art

Tilmicosin is a semi-synthetic macrolide antibiotic that is approved for veterinary use in cattle and swine to combat respiratory disease in the US, and in Canada for the treatment of pneumonia in lambs. Bovine respiratory disease associated with *Mannheimia (Pasteurella) haemolytica* can be treated and controlled by a single subcutaneous injection of tilmicosin. Tilmicosin also has in vitro activity against several gram-negative bacteria associated with respiratory disease, including *Actinobacillus pleuropneumoniae, Pasteurella multocida, P. haemolytica,* and Mycoplasma spp. The administration of tilmicosin may also be a convenient way to reduce mastitis infection.

Tilmicosin is derived from the macrolide antibiotic tylosin, produced by *Streptomyces fradiae.* Synthesis of tilmicosin was described by Debono et al. (U.S. Pat. No. 4,820,695). Briefly, in a two step process, tylosin is first hydrolyzed to yield desmycosin, which is then treated with dimethyl piperidine to produce tilmicosin.

It is known that most antimicrobial agents have limited ability for cellular penetration. However, tilmicosin has been shown to concentrate in bovine lung tissue. Even after serum levels have dropped below therapeutic concentrations, lung concentrations have been shown to exceed the *P. haemolytica* MIC for at least 72 hours after dosage.

Attempts have been made to produce a quick and economical competitive enzyme-linked immunosorbent assay (cELISA) method for determining tilmicosin residues in feeds and tissues. Jackman et al. (1997, J. Vet. Pharmacol. Therap., 20 (suppl. 1):131–132) reported the preparation of polyclonal antibodies to tilmicosin using desmycosin and lactenocin conjugated to carrier proteins. Silverlight et al. (1999, Food and Agricultural Immunology, 11:321–328) later reported that the antibodies raised against desmycosin and lactenocin conjugates bound both tilmicosin and tylosin. However, tilmicosin could not be used in an immunogenic preparation.

Despite these advances, the need persists for a monoclonal antibody to tilmicosin having improved sensitivity and specificity.

SUMMARY OF THE INVENTION

We have now discovered hybridoma cell lines which produce and secrete monoclonal antibodies which selectively bind to tilmicosin. We have unexpectedly found that these hybridomas may be obtained by using as an immunization agent or immunogen, 23-deoxo-23-demycinosyl tilmicosin which has been conjugated to an immunogenic carrier. Tilmicosin in biological samples may be detected and quantified by contacting the sample with the antibodies to form a tilmicosin/antibody immunocomplex when tilmicosin is present, which immunocomplex may then be detected. The monoclonal antibodies also may be incorporated into kits for the detection and quantification of tilmicosin.

It is an object of this invention to provide hybridoma cell lines that produce and secrete high affinity monoclonal antibodies which selectively bind to tilmicosin.

A further object of this invention is to provide monoclonal antibodies which selectively bind to tilmicosin but not tylosin.

Another object of this invention is to provide immunoassay methods for the measurement of tilmicosin in biological samples.

A further object is to provide kits useful for the assay of tilmicosin which include the monoclonal antibodies described herein.

Yet another object is to provide an immunization agent which may be used to produce hybridoma cell lines that produce and secrete high affinity monoclonal antibodies which selectively bind to tilmicosin.

Other objects and advantages of this invention will become readily apparent from the ensuing description.

DETAILED DESCRIPTION OF THE INVENTION

In accordance with this invention we have created hybridoma cell lines that produce monoclonal antibodies that bind tilmicosin and are effective for detecting and quantifying levels of this antibiotic. We have unexpectedly discovered that by use of a novel immunogen, monoclonal antibodies may be produced which possess improved specificity and increased affinity for tilmicosin. The antibodies of this invention may be used to rapidly and accurately detect and quantify tilmicosin, providing an indicator of the level of this antibiotic in biological samples.

Traditionally, preparation of hybridomas may be accomplished using conventional techniques such as described by Kohler and Milstein [Nature, 256:495–497 (1975)], Koprowski et al. [U.S. Pat. No. 4,196,265], Wands [U.S. Pat. No. 4,271,145], or Stanker et al. [U.S. Pat. No. 5,466,784], the contents of each of which are incorporated by reference herein. Briefly, the process of preparation comprises the steps of immunizing an animal with the antigen of interest, recovering splenocytes or lymphocytes from the animal, fusing the splenocytes or lymphocytes with continuously replicating myeloma cells to produce hybrid cells, and screening the resultant hybrid cells for the production of antibodies to the antigen.

Often, the compound of interest is a relatively small molecule, and hence is itself incapable or only poorly capable of stimulating the immune system to produce antibodies. To render such compounds immunogenic, they are generally conjugated to an immunogenic carrier in such a manner that the resultant immunogen is capable of stimulating the immune system of an animal to produce specific antibodies that are capable of binding the unconjugated compound. Application of this traditional protocol for the generation of monoclonal antibodies to a small compound such as tilmicosin, would logically dictate an immunogen prepared by conjugation of tilmicosin to a carrier protein. However, in a departure from established practice, we describe here the preparation of monoclonal antibodies using significantly different, novel immunogens.

The method of preparing the hybridomas comprises the following steps:

Immunogen. The immunization agent of this invention is not constructed from tilmicosin, but is derived from 23-demycinosyl tilmicosin (which may also be referred to as 20-deoxo-20-[3,5-dimethyl-piperidin-1-yl]desmycosin). The structures of tilmicosin and 23-demycinosyl tilmicosin are shown in formulas I and II, respectively:

(I)

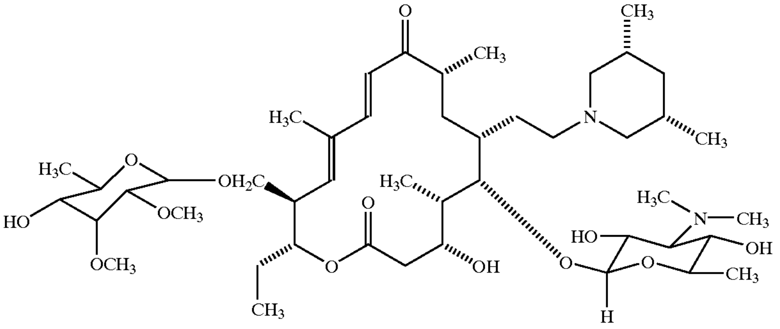

(II)

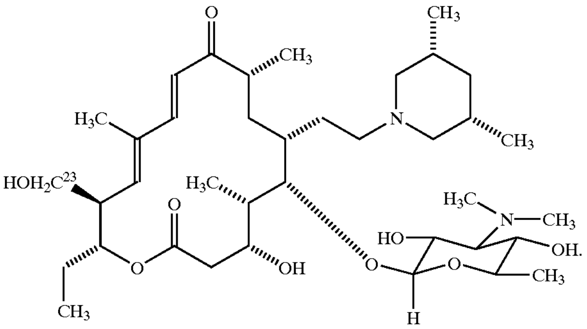

The immunization agent is prepared by covalently conjugating an immunogenic carrier to 23-deoxo-23-demycinosyl tilmicosin at carbon atom number 23 thereof. Immunogenic carriers are defined herein as any compound to which the haptens may be attached to render them immunogenic. Suitable carriers are well known and may be readily determined by the practitioner skilled in the art. Without being limited thereto, preferred carriers include proteins such as keyhole limpet hemocyanin (KLH), bovine serum albumin (BSA), ovalbumin, glucose oxidase, and human thyroglobulin.

The immunogenic carrier may be conjugated to the 23-deoxo-23-demycinosyl tilmicosin molecule directly or through an optional crosslinking agent or spacer. In accordance with the preferred embodiment, the immunogen is created by conjugating the carrier to 23-deoxo-23-demycinosyl tilmicosin which has been modified by reaction at the $C^{23}$ thereof with a crosslinking agent. A variety of diamine crosslinking agents are suitable for use herein, with diamino hydrocarbons and/or thiols being preferred. Suitable diamino hydrocarbons include, but are not limited to straight or branched chain, cyclic, saturated or unsaturated, diamino hydrocarbons, such as 1,3-diaminopropane, 1,4-diaminobutane, or hexamethylenediamine.

In a particularly preferred embodiment which is described in greater detail in Example 1, to selectively bind the crosslinking agent to $C^{23}$ of the hapten, the $C^{23}$ of 23-demycinosyl tilmicosin (II) is first halogenated, for example, by treatment with $Cl_2$, $F_2$, or $Br_2$, and preferably $I_2$. In this initial reaction, only the $C^{23}$ is halogenated to a significant degree, with the hydroxyl group of 23-demycinosyl tilmicosin being displaced by the halogen to yield 23-halo-23-deoxo-23-demycinosyl tilmicosin of the formula (III):

(III)

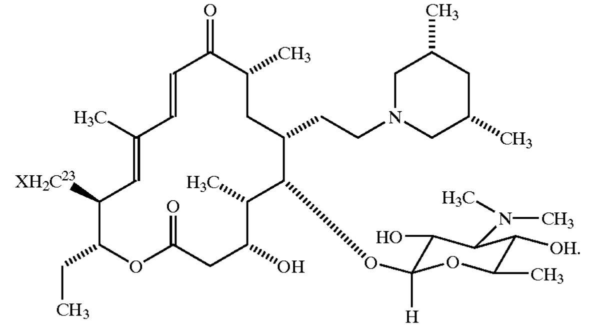

The other hydroxyl groups of the 23-demycinosyl tilmicosin are not displaced to any significant degree. Following this displacement reaction, (III) may then be reacted with the diamino hydrocarbon $H_2N—R—NH_2$, with the halide being in turn displaced by the amine, yielding 23-diamino-23-deoxo-23-demycinosyl tilmicosin of the formula (IV):

(IV)

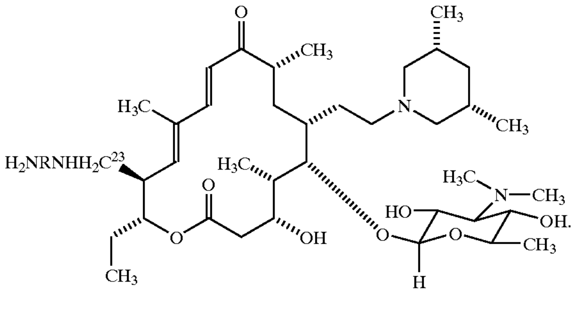

The carrier protein may be directly conjugated to the terminal amine of (IV) using techniques known in the art. However, in the preferred embodiment, the terminal amine of (IV) is first displaced with a thiol such as described in Example 1, which may be more readily conjugated to the carrier protein.

In an alternative reaction, it is also envisioned that the carrier may be conjugated directly to 23-deoxo-23-demycinosyl tilmicosin without use of a crosslinking agent. For instance, without being limited thereto, 23-halo-23-deoxo-23-demycinosyl tilmicosin (III) may be reacted with carrier protein, with the halide being displaced by an amine of the protein.

In yet another alternative embodiment, 23-thiol-23-deoxo-23-demycinosyl tilmicosin may be prepared by displacement of the halide of (III) by a thiol, which thiol may then be conjugated to the carrier protein. In this embodiment, the thiol is effective as an alternative crosslinking agent.

Immunogens of this invention prepared by conjugation of 23-deoxo-23-demycinosyl tilmicosin to a carrier protein through a crosslinking agent may be generally described by the formula (V):

(V)

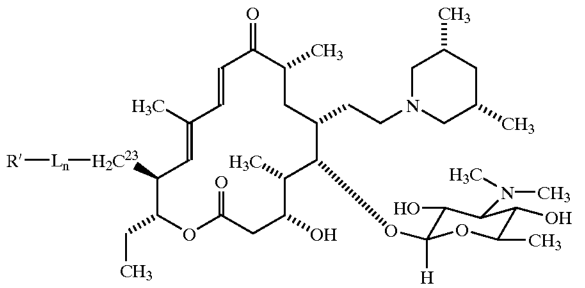

wherein L refers to the optional crosslinking agent, and R' is a carrier protein.

Immunization. To generate antibody-producing splenocytes or lymphocytes, an immunizing preparation comprising the 23-deoxo-23-demycinosyl tilmicosin-carrier complex is injected into an immunologically competent animal. The preparation may also contain other proteins, although pure or partially pure compositions of the conjugate in a pharmaceutically acceptable carrier are preferred.

Without being limited thereto, rats and particularly mice are preferred animals for immunization because of ease of handling. Preparation of hybridomas using splenocytes from these animals fused to a variety of myeloma cell lines have been reported by many investigators.

Inoculations of the animal can be by various routes. A series of three inoculations, generally at two week intervals, with a composition of the complex in isotonic saline with RIBI adjuvant (Immunochem Research, Inc., Hamilton, Mont.) elicits good antibody response, and is preferred. The skilled practitioner will recognize that other routes of administration, immunization schedules, and carriers or adjuvants may be used.

Hybridization. Splenocytes or lymphocytes recovered from the immunized animal are fused with continuously replicating tumor cells, such as myeloma or lymphoma cells, cultured, and hybridoma cells selected. Many continuously replicating tumor cell lines are available which may be used as fusion partners with the splenocytes. Without being limited thereto, preferred myeloma cells include P3-NS1-K653, and particularly SP2/O.

Fusion and culture of the cells can be performed using conventional techniques. In accordance with one well-known effective procedure, the splenocytes and myeloma cells are fused by exposure to polyethylene glycol. Hybrid cells are selected by culture in hypoxanthine-aminopterin-thymidine (HAT) medium, whereby unfused myeloma cells are killed by HAT and splenocytes die out, leaving only the hybrid cells. The resultant hybridomas are then grown in HAT or other suitable culture medium and assayed for antibody production.

Screening. Samples of the supernatant culture fluid from the hybridomas are screened for antibodies to tilmicosin. In accordance with the preferred embodiment, the supernatants are screened using a modification of the direct-binding ELISA (db-ELISA). In this embodiment, solid substrates, such as beads or the wells of a microtiter plate which have been coated with tilmicosin-, or most preferably, 23-deoxo-23-demycinosyl tilmicosin-carrier complex, are used to bind anti-tilmicosin antibody in the supernatants, and bound antibody is then detected.

Following contact of the supernatant culture fluid with the tilmicosin or 23-deoxo-23-demycinosyl tilmicosin coated substrate, detection of bound antibody may be accomplished by addition of enzyme-labeled anti-immunoglobulin antibodies followed by enzyme substrate. While a variety of enzyme/substrate labels may be used, horse radish peroxidase and its substrate, 2,2'-azinobis-3-ethylbenthiazolinesulfonic acid (ABTS) are preferred. In the alternative, it is understood that the supernatants also may be screened using non-enzyme labels, such as radiolabels or chromophores, in related solid-phase immunosorbent techniques such as RIA and FIA.

Cloning. Cloning of hybridomas which are positive for desired antibody production can be carried out as soon as they are detected by any method known in the art. Hybridomas having a positive response in the ELISA screen are preferably expanded and subcloned one or more times by limiting dilution to assure monoclonality.

The supernatant culture fluid from the cloned hybridomas also may be screened to select for those producing antibodies having a high affinity for tilmicosin. Affinity may be measured using solid phase immunoassays such as ELISA, RIA, or equilibrium dialysis using labeled tilmicosin. In the preferred embodiment, affinity is measured by competitive indirect ELISA as described in the Examples, and is conducted at a final antibody concentration (dilution from the tissue culture supernatant) to give 50% of maximal binding to a tilmicosin- or 23-deoxo-23-demycinosyl tilmicosin-carrier complex coated substrate or assay well (i.e., the concentration of the antibody that results in 50% of the plateau activity in direct binding ELISA). In accordance with this embodiment, the antibody containing supernatant is added to a tilmicosin or 23-deoxo-23-demycinosyl tilmicosin coated substrate such as the wells of a microtiter plate (prepared as described above), together with a range of concentrations of free tilmicosin as a competitor. Following incubation and washing, bound antibody in the wells is determined in the same manner as the db-ELISA. Percent inhibition may be calculated as $(1-B/B_o)\times100$, where B is the optical density (OD) of a well with a competitor and $B_o$ is the mean OD of the wells without competitor (control). The relative affinity of the antibodies may be accurately measured as the concentration of tilmicosin added to the wells that results in at least 20% inhibition ($IC_{20}$) of control activity. However, for greater accuracy, the affinity may be alternatively measured at 50% inhibition ($IC_{50}$). In addition to screening the hybridomas for those producing monoclonal antibodies having a high affinity for tilmicosin, the hybridomas may also be screened to select those producing antibodies which do not significantly bind to the related antibiotic, tylosin. As defined herein, antibodies which do not significantly bind to tylosin are those which do not exhibit any observable binding to tylosin at levels of 1,000 ng/well. Alternatively, although the hybridomas described in the Examples produce antibodies which do not bind to tylosin, it is envisioned that hybridomas produced in accordance with this invention may be screened for those producing antibodies which do bind to tylosin.

Once hybridomas producing and secreting the desired anti-tilmicosin antibodies are identified, large quantities of the antibodies may be produced in tissue culture using well-known techniques. In a preferred embodiment, the antibodies are produced in vitro in modular mini fermentors, as described by Falkenberg et al. (1995, J. Immunol. Methods, 179:13–29; and 1998, Res. Immunol., 149:560–570). Alternatively, antibodies may be produced within host animals, such as by ascites formation in syngenic mice. Monoclonal antibodies so produced may be purified, for example, by affinity chromatography on a protein A or G resin, or using tilmicosin bound to a resin.

The monoclonal antibodies produced in accordance with this invention possess high affinity for tilmicosin, allowing the rapid determination of these agents at low levels. As described in detail in the Examples, when the sensitivity was measured at a high standard of accuracy ($IC_{20}$) by competitive inhibition ELISA, the detection limits of the antibodies for tilmicosin was as low as 0.85 ng.

The antibodies may be used to detect and/or quantify tilmicosin in unknown samples using a variety of conventional immunosorbent assays including but not limited to RIA, FIA or ELISA. A competitive inhibition ELISA similar to that used to screen the hybridomas is preferred. In this assay, a sample to be analyzed is incubated with the monoclonal antibody for tilmicosin and a solid substrate coated with tilmicosin, tilmicosin-carrier complex, 23-deoxo-23-demycinosyl tilmicosin, 23-deoxo-23-demycinosyl tilmicosin-carrier complex, 3,5-dimethyl piperidine, or 3,5-dimethyl piperidine-carrier complex. The hapten coated substrate and any free tilmicosin in the sample thus compete for binding with the antibody. After incubation, the solid phase is drained and washed, and bound antibody on the substrate is detected and percent inhibition calculated as described earlier. The concentration of tilmicosin in the sample may then be determined by reference to a standard curve constructed from assays using known levels of tilmicosin.

In one alternative embodiment, tilmicosin may be determined by a competition ELISA such as described in Brandon et al. (U.S. Pat. No. 5,053,327, the contents of which are incorporated by reference herein) using the monoclonal antibody of the invention attached to a solid support. For example, the anti-tilmicosin antibody may be immobilized on a solid support such as a bead or microtiter well. The unknown sample to be analyzed (or analytical standards of tilmicosin) are then added with enzyme or radiolabeled tilmicosin, and the amount of labeled tilmicosin bound to the antibody is measured, using a substrate when the label is an enzyme. The amount of tilmicosin in the sample is inversely proportional to the amount of bound labeled tilmicosin. In another alternative, the monoclonal antibody may be attached to a solid support for use in conventional double-antibody sandwich ELISA procedures.

With any of the above-described assay formats, the monoclonal antibodies of the invention may be incorporated into kits, alone or preferably together with any other necessary reagents. A preferred kit for use herein comprises a first container including the monoclonal antibody, a second container including detection means effective for detecting bound antibody, and a solid phase support having tilmicosin or 23-deoxo-23-demycinosyl tilmicosin attached thereto.

Determination of tilmicosin in a variety of feeds or biological samples, including animal tissue and animal fluids such as serum, may be conducted using the above-described assays with minimal sample preparation and using simple extraction procedures. For the analysis of tissue samples, the tissue may be homogenized in buffer, such as Tris-HCl, centrifuged, and the liquid phase recovered and used directly in the immunoassay. alternatively, tissue may be probed directly by application of labeled antibody onto the tissue to bind any tilmicosin therein or thereon, and antibody-tilmicosin complex detected as described above. Although any animal tissue may be analyzed, the assay is particularly valuable for the determination of tilmicosin in meats. Tissue for analysis in accordance with the invention may originate from virtually any animal. Without being limited thereto, the assays are preferably used for the analysis of feeds and tissue samples and meats from domestic animals, particularly bovine, porcine, and ovine, most particularly, cattle, swine, and sheep.

Another application of the monoclonal antibodies is affinity purification of tilmicosin. The antibodies may be bound to a matrix, column, or other support using well-known techniques and used to recover or remove tilmicosin from any desired material. Alternatively, the monoclonal antibodies may be incorporated into sensors such as solid phase electronic devices for detection of tilmicosin in sample materials.

The following examples are intended only to further illustrate the invention and are not intended to limit the scope of the invention which is defined by the claims.

EXAMPLE 1

Immunogen and Plate Coating Antigen Production

Different methods were used to produce the injection antigen and the plate coating conjugate. Using different methods of linking results in different linker arms providing a heterologous assay that is free from unwanted cross-reactivity.

Hapten Production

Production of the hapten with the linker arm requires a diamino- derivative of 23-deoxo-23-demycinosyl tilmicosin [i.e., 20,23-dideoxo-20-(3,5-dimethyl-piperidin-1-yl) desmycosin]. To arrive at the correct intermediate the Wallach reaction may be used on 23-demycinosyl-tylosin (DMT), similar to that used on tylosin in the paper by Debono et al. (1989, J. Antibiot., 42:1253–1267). Although the 23-demycinosyl tylosin starting material may be chemically synthesized using well-known techniques, it is preferably prepared by fermentation with mutant strains of *S. fradiae* as described by Baltz (U.S. Pat. No. 4,321,361), Kirst et al. (1983, J. Antibiotics, 36:376–382), and Okamoto et al. (1982, J. Antibiotics, 35:921–924), the contents of each of which are incorporated by reference herein. In the process of this invention, heat 23-demycinosyl-tylosin, of formula (VI):

(VI)

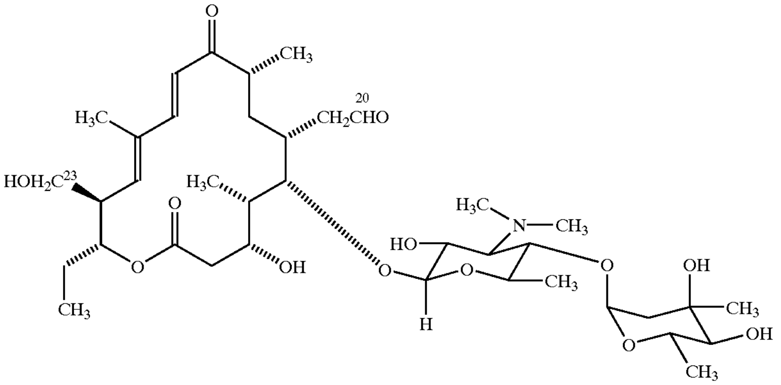

in water (400 mg/mL, 18.55 mL, 0.01 mol) slowly to 35° C. while adjusting the pH to 1.6 with $H_2SO_4$. Cool reaction mixture after heating for 1 hr. Add amyl acetate (20 mL) to mixture, and adjust pH to 11 with 5 N NaOH. The amyl acetate layer is separated. Add 3,5-dimethylpiperidine (1.13 g, 0.01 mol) to the amyl acetate solution at room temperature, and heat the mixture to 70° C. Add formic acid (96%, 0.502 g, 0.0105 mol) in amyl acetate (5 mL) to the heated amyl acetate solution. Cool the reaction mixture to room temperature after 2 hrs. Add water (25 mL) and adjust the pH to 4.5 with concentrated HCl. Separate the aqueous layer and dilute with water (175 mL). Stir the solution at room temperature, and raise its pH to 11 by addition of 5 N NaOH. Remove the remaining precipitate by filtration, wash with water and vacuum dry at room temperature to afford 23-demycinosyl tilmicosin [i.e., 20-deoxo-20-(3,5-dimethyl-piperidin-1-yl)desmycosin] shown in formula (VII):

(VII)

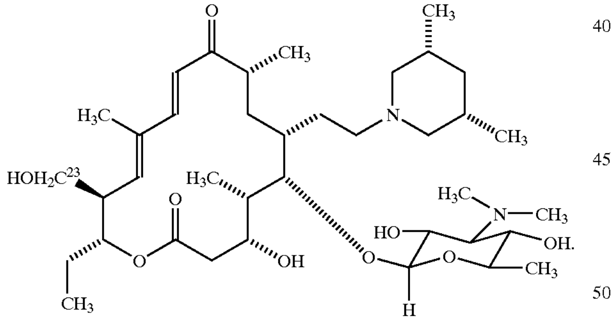

The next intermediate required is the 23-iodo of 23-demycinosyl tilmicosin. To arrive at the 23-iodo intermediate, a modified method of Sakamoto et al., *Bull. Chem. Soc. Jpn.* 57:3536–3542 (1984) may be used. Dissolve (VII) (0.42 g, 0.6065 mmol) in anhydrous pyridine (3 mL), and then dissolve triphenylphosphine (0.32 g, 1.22 mmol) (2×). Add 4 Å molecule sieves and stir under dry argon gas for 1.25 hr. Solubilize $I_2$ (0.462 g, 1.82 mmol) (3×) in anhydrous pyridine. Place the reaction flask in an ice bath. Add the $I_2$ solution dropwise through a septum on the Reaction flask until the reaction mixture color turns brown. Stir the reaction mixture for 1.25 hr in the ice bath and 1 hr at room temperature. Filter the reaction mixture through a double layer of Whatman #2 and #41 filter paper with the aid of $CH_2Cl_2$ to remove the 4 Å molecular sieve material. Extract the filtrate with a saturated solution of $NaHCO_3$ (75 mL) and $CH_2Cl_2$ (40 mL). Extract two more times with $CH_2Cl_2$ (30 mL). Combine the $CH_2Cl_2$ layers and extract with 1 M sodium thiosulfate (80 mL). Extract the water layer twice more with $CH_2Cl_2$ (30 mL). Dry the combined $CH_2Cl_2$ layers over sodium sulfate to afford the required 23-iodo-23-deoxo-23-demycinosyl tilmicosin [i.e., 23-iodo-20,23-dideoxo-20-(3,5-dimethyl -piperidin-1-yl) desmycosin] shown in Formula (VIII):

(VIII)

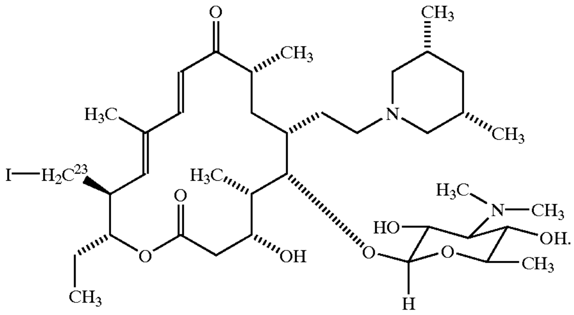

The next intermediate is the required 23-amine of (VIII) that is used to both produce the immunizing and plate coating antigens. The method used to produce the 23-(1,3-diaminoprop-1-yl) compound is similar to that found in the paper by Debono et al. (1989, J. Antibiot., 42:1253–1267). Dissolve (VII) (0.488 g, 0.6065 mmol) in ACN (5 mL). Add $K_2CO_3$ (167.6 mg, 1.213 mmol) (2×) to the reaction mixture. Add 1,3-diaminopropane 125.1 mg, 1.69 mmol) (5×) to the reaction mixture. Stir the mixture at 60° C. for 24 hr. Cool the reaction mixture to room temperature and filter the mixture through a double layer of Whatman #2 and #41 filter paper with the aid of $CH_2Cl_2$ to remove the potassium carbonate. Rotoevaporate the filtrate to remove the ACN. Dissolve the residue (glass) with $CH_2Cl_2$ (40 mL) and extract with saturated $NaHCO_3$ (75 mL). Extract the water layer two more times with $CH_2Cl_2$ (30 mL). Extract the combined $CH_2Cl_2$ layers with pH 3 buffer (100 mL). Wash the buffer layer 3 times with $CH_2Cl_2$ (40 mL). Raise the pH of the buffer layer to 10 with 4 N NaOH. Extract the pH 10 layer with $CH_2Cl_2$ (40 mL) and twice with $CH_2Cl_2$ (30 mL). Combine $CH_2Cl_2$ layers, dry over sodium sulfate, filter through Whatman #41 filter paper, and rotoevaporate to dryness to afford 23-(1,3-diaminoprop-1-yl)-23-deoxo-23-demycinosyl tilmicosin [i.e., 23-(1,3-diaminoprop-1-yl) -20, 23-dideoxo-20-(3,5-dimethyl-piperidin-1-yl)desmycosin] shown in formula (IX):

(IX)

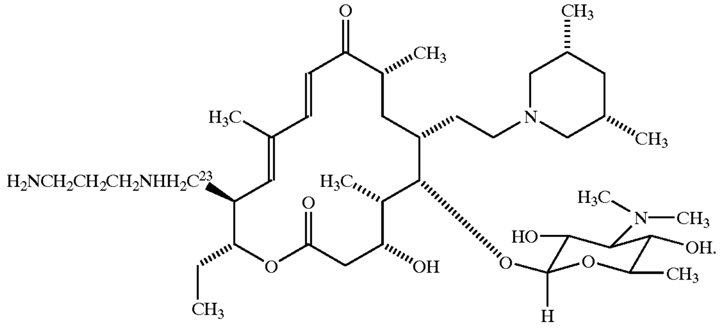

Thio-maleimide/KLH conjugate of Hasten for Injection Antigen

To complete the linker, and conjugate the hapten with KLH, compound (IX) was reacted with Traut's reagent. This process extends the linker arm and terminates with a reactive -SH group. Dissolve (IX) (86% purity, 1.82 mg, 2.423 $\mu$mol) with DMSO (30 $\mu$L) and then add phosphate buffer (190 $\mu$L) pH 7.2. (Note: all solvents used, phosphate buffer pH 7.2, DMSO, and $H_2O$ were deaerated with argon gas, and stored in a septum sealed flask under argon gas.) Traut's reagent (0.3 mg, 30 $\mu$L of a 1 mg/100 $\mu$L solution, 2.35 $\mu$mol) was added. The solution was stirred for 1 hr in the absence of light to afford the activated sulphahydryl containing hapten shown in formula (X):

(X)

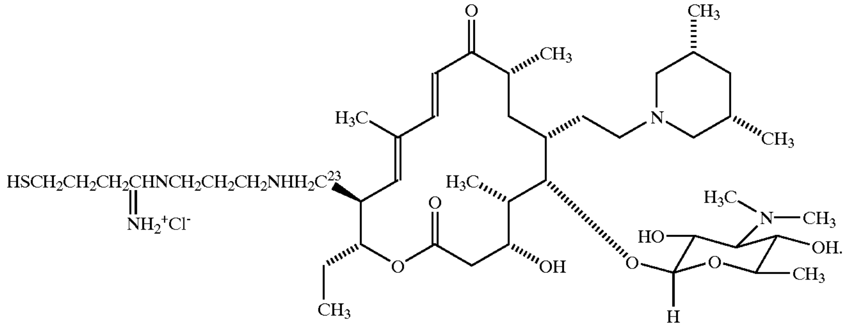

Dissolve maleimide activated KLH (2 mg) with argon treated $H_2O$ (200 $\mu$L), and transfer the KLH solution to the above completed Traut's reaction (two-25 $\mu$L aliquots of the phosphate buffer pH 7.2 was used to make the transfer). Stir the reaction mixture for 2 hr at room temperature. The reaction mixture was split in two and the protein was separated from the salts on two NAP 5 columns from Pharmacia Biotech. After the NAP 5 columns were equilibrated with Imject Purification Buffer (10 mL each) (No, 77159, Pierce, Rockford, Ill.) and when the buffer completely entered the column bed, then the samples (0.5 mL each) were placed on the column. When the samples completely entered the beds, they were then eluted with the Imject Purification Buffer (1 mL each) to afford a solution of the conjugated hapten-KLH ready to use for injection. This immunogen is shown in formula (XI):

(XI)

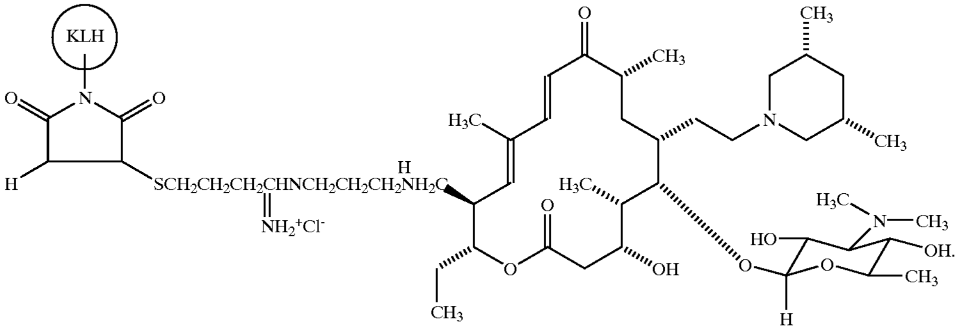

Further reaction was completed with maleimide activated BSA. It was determined that there were 22 thio-residues per BSA molecule.

EDC/BSA Conjugate of Hapten Used for Plate Coating

To prepare plate coating antigen, add 3 mg BSA to 0.1 M MES (2-[N-morpholino]ethane sulfonic acid) (300 μL) pH 5 (coupling buffer). Dissolve 23-(1,3-diaminoprop-1-yl)-23-deoxo -23-demycinosyl tilmicosin (IX) prepared as above (5.856 mg, 7.8 μmol) in coupling buffer (550 μL). Transfer the BSA solution to the hapten solution. Dissolve EDC (12.8 mg) in coupling buffer (1.28 mL), and immediately add 150 μL of the solution to the reaction mixture. The reaction was stirred for 2 hrs at room temperature. Two NAP 5 Columns were equilibrated with Pierce purification buffer (10 mL each). The reaction mixture was split into two 0.5 mL portions. Each portion was allowed to fully enter the column bed of the respective NAP 5 column. Each column was eluted with the purification buffer (1 mL). The solutions resulted in a protein concentration of 1.827 mg/mL. The structure of the resultant plate coating antigen is shown in formula (XII):

(XII)

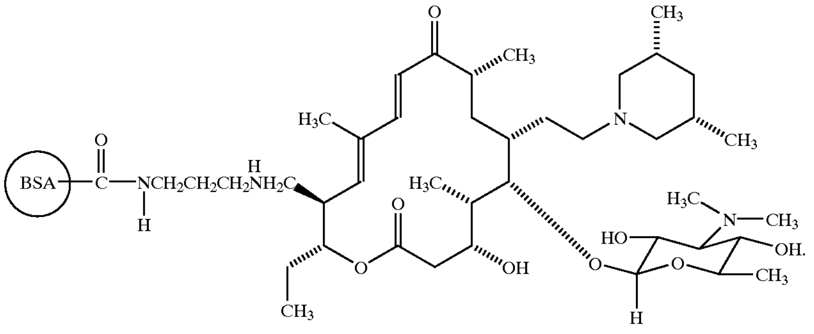

Plates are coated with 75 ng of (XII) per well.

EXAMPLE 2

Hybridoma Production

Immunization Protocol and Hybridoma Production.

Animal immunization and hybridoma production substantially followed the protocols described in Stanker et al. (U.S. Pat. No. 5,908,781), the contents of which are incorporated by reference herein.

Antibodies and ELISA Methods.

Standard indirect ELISA and competitive-indirect ELISA ciELISA) methods were used for screening which also substantially followed the protocols described in Stanker et al. (U.S. Pat. No. 5,908,781), except that 23-deoxo-23-demycinosyl tilmicosin- carrier complex (XII) was immobilized on 96-well microtiter plates, and free tilmicosin was used as a competitor. The same antigen coated plates were used for all screening procedures.

The cells which were positive in the initial screening and expanded were analyzed by competitive indirect ELISA (ciELISA) below for inhibition of antibody binding in the presence of free (unconjugated) tilmicosin on (XII) coated antigen plates. Similar ciELISA assays were conducted using different competitors, including free tylosin. Six of the 144 original cell cultures which produced antibodies whose binding was inhibitable by free tilmicosin but not tylosin, were subcloned resulting in the establishment of six stable monoclonal cell lines secreting anti-tilmicosin antibodies. These hybridoma cell lines were designated as follows: 37-4-5, 37-2-6, 47-1-1, 9-7-7, 9-1-4, and 9-5-3. The results for these six antibodies are shown in Table 1:

| | Antibody (pmol/well, % Competition[a]) | | | | | |
|---|---|---|---|---|---|---|
| Compound | 37-4-5[b] | 37-2-6 | 47-1-1 | 9-7-7 | 9-1-4[b] | 9-5-3 |
| Tilmicosin | 11.5, 100 | 10.7, 100 | 7.7, 100 | 10.4, 100 | 7.6, 100 | 25.3, 100 |
| Tylosin | —[c] | — | — | — | — | — |
| Hapten (VIII) | 13.3, 86 | 18.6, 58 | 18.6, 41 | 20.0, 52 | 20.0, 38 | 17.3, 146 |
| 3,5-dimethyl piperidine | 61.8, 19 | 44.2, 24 | 44.2, 17 | 40.6, 26 | 41.5, 18 | 35.3, 72 |
| Piperidine | —[c] | — | — | — | — | — |
| 1-methyl piperidine | — | — | — | — | — | — |
| 2-methyl piperidine | — | — | — | — | — | — |
| 3-methyl piperidine | — | — | — | — | — | — |
| 4-methyl piperidine | — | — | — | — | — | — |
| 2,6-dimethyl-piperidine | — | — | — | — | — | — |
| 1-piperidineethanol | — | — | — | — | — | — |

[a]Percentage of cross-reactivity was calculated according to the formula: ($IC_{50}$ of Tilmicosin)/($IC_{50}$ of other Compound) X100.
[b]Hybridomas deposited with ATCC.
[c]No cross-reactivity was observed.

Two of the cell lines, 37-4-5 (also referred to as Til-1) and 9-1-4 (also referred to as Til-5) have been deposited under the Budapest Treaty in the American Type Culture Collection (10801 University Blvd., Manassas, Va., USA) on Sep. 20, 2001, and have been assigned accession numbers ATCC PTA-3715 and PTA-3714, respectively. The lowest observable detection limits for the antibodies from these deposited cell lines, measured at 20% inhibition of control activity ($IC_{20}$) was 2.36 ng tilmicosin/well for Til-1 (SDV=1.92), and 0.85 ng tilmicosin/well for Til-5 (SDV=0.55).

It is understood that the foregoing detailed description is given merely by way of illustration and that modifications and variations may be made therein without departing from the spirit and scope of the invention.

I claim:

1. A hybridoma cell line which produces and secretes monoclonal antibodies which selectively bind to tilmicosin, which is produced using an immunization preparation comprising 23-deoxo-23-demycinosyl tilmicosin conjugated to an immunogenic carrier.

2. The hybridoma cell line of claim 1 wherein said 23-deoxo-23-demycinosyl tilmicosin is conjugated to said immunogenic carrier through the $C^{23}$ of said 23-deoxo-23-demycinosyl tilmicosin.

3. The hybridoma cell line of claim 2 wherein said immunogenic carrier is a protein.

4. The hybridoma cell line of claim 2 wherein said immunization preparation further comprises a crosslinking agent between said immunogenic carrier and said $C^{23}$ of said 23-deoxo-23-demycinosyl tilmicosin.

5. The hybridoma cell line of claim 4 wherein said crosslinking agent is selected from the group consisting of diamino hydrocarbons and a thiol.

6. The hybridoma cell line of claim 1, wherein said cell line is selected from the group consisting of Til-1 and Til-5.

7. A monoclonal antibody produced by the hybridoma cell line of claim 1.

8. A monoclonal antibody produced by the hybridoma cell line of claim 2.

9. A monoclonal antibody produced by the hybridoma cell line of claim 4.

10. A monoclonal antibody produced by the hybridoma cell line of claim 6.

11. A method for detecting tilmicosin in a biological sample comprising:

(a) providing a sample of biological material; and (b) subjecting said sample to an immunosorbent assay using a monoclonal antibody which selectively binds to tilmicosin and which is produced by the cell line of claim 1, said monoclonal antibody forming an immunocomplex with tilmicosin when said tilmicosin is present, and (c) detecting said immunocomplex, wherein the detection of said immunocomplex indicates the presence of tilmicosin in said biological sample.

12. The method of claim 11 wherein said cell line is elected from the group consisting of Til-1 and Til-5.

13. The method of claim 11 wherein said sample is selected from the group consisting of feeds, animal tissue, and animal fluids.

14. The method of claim 13 wherein said sample is tissue from an animal selected from the group consisting of bovine, porcine, and ovine.

15. The method of claim 11 wherein said immunosorbent assay comprises:

(a) providing a solid substrate having tilmicosin, tilmicosin-carrier complex, 23-deoxo-23-demycinsosyl tilmicosin, 23-deoxo-23-demycinsosyl tilmicosin-carrier complex, 3,5-dimethyl piperidine, or 3,5-dimethyl piperidine-carrier complex bound thereto;

(b) contacting said sample with said solid substrate and said monoclonal antibody;

(c) washing said support;

(d) detecting any monoclonal antibody bound to said support; and (e) determining the presence of tilmicosin in said sample.

16. The method of claim 11 wherein said immunosorbent assay is a competitive inhibition assay comprising:

(a) providing a solid substrate having a first hapten conjugated to a carrier bound thereto, said first hapten being selected from the group consisting of tilmicosin, tilmicosin-carrier complex, 23-deoxo-23-demycinsosyl tilmicosin, 23-deoxo-23-demycinsosyl tilmicosin-carrier complex, 3,5-dimethyl piperidine, and 3,5-dimethyl piperidine-carrier complex;

(b) contacting said sample with said solid substrate and said monoclonal antibody, wherein said monoclonal antibody may bind with either said first hapten on said support or with tilmicosin in said sample;

(c) washing said support;

(d) detecting any monoclonal antibody bound to said first hapten on said support; and (e) determining the presence of tilmicosin in said sample.

17. A kit for the detection or quantification of tilmicosin in a biological sample comprising a monoclonal antibody which selectively binds to tilmicosin and which is produced by the hybridoma cell line of claim 1.

18. The kit of claim 17 wherein said cell line is selected from the group consisting of Til-1 and Til-5.

19. An immunogen comprising 23-deoxo-23-demycinosyl tilmicosin conjugated to an immunogenic protein and which is of the formula:

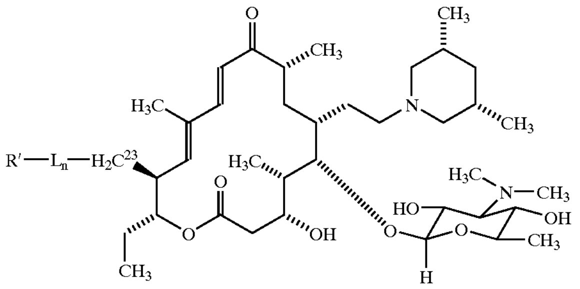

wherein R' is said immunogenic protein, and L is a crosslinking agent, and n is 0 or 1.

* * * * *